(12) United States Patent
Shang et al.

(10) Patent No.: US 8,241,706 B2
(45) Date of Patent: Aug. 14, 2012

(54) HIGH SURFACE AREA CERAMIC COATED FIBERS

(75) Inventors: Jian-Ku Shang, Champaign, IL (US); Rongcai Xie, Urbana, IL (US); Zhongren Yue, Urbana, IL (US); James Economy, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/876,011

(22) Filed: Sep. 3, 2010

(65) Prior Publication Data

US 2011/0064609 A1     Mar. 17, 2011

Related U.S. Application Data

(63) Continuation of application No. 10/797,582, filed on Mar. 10, 2004, now abandoned.

(51) Int. Cl.
*B05D 3/02* (2006.01)
(52) U.S. Cl. .................................................. 427/376.1
(58) Field of Classification Search ................ 427/376.1
See application file for complete search history.

(56) References Cited

U.S. PATENT DOCUMENTS

| | | |
|---|---|---|
| 2,670,334 A | 2/1954 | D'Alelio |
| 2,877,142 A | 3/1959 | Rusher et al. |
| 2,885,366 A | 5/1959 | Iler |
| 3,373,104 A | 3/1968 | Ryan |
| 3,395,970 A | 8/1968 | Machell |
| 3,518,206 A | 6/1970 | Stiles et al. |
| 3,520,805 A | 7/1970 | Ryan |
| 3,542,582 A | 11/1970 | Degginger |
| 3,592,834 A | 7/1971 | Buckman et al. |
| 3,676,173 A | 7/1972 | Adams |
| 3,723,588 A | 3/1973 | Economy et al. |
| 3,799,796 A | 3/1974 | Hunter |
| 3,853,721 A | 12/1974 | Darlington et al. |
| 3,903,220 A | 9/1975 | Economy et al. |
| 3,946,061 A | 3/1976 | Buckman et al. |
| 3,956,185 A | 5/1976 | Yagi et al. |
| 3,971,669 A | 7/1976 | Wrzesien et al. |
| 4,039,716 A | 8/1977 | Johnson |
| 4,045,338 A | 8/1977 | Miyamoto et al. |
| 4,100,314 A | 7/1978 | Wallouch |
| 4,125,486 A | 11/1978 | Uzumaki et al. |

(Continued)

FOREIGN PATENT DOCUMENTS

DE     3339756 A1     5/1985

(Continued)

OTHER PUBLICATIONS

Ban et al "Photocatalysis of a Transparent Titanate Aqueous Sol Prepared from Titanium Tetraisopropoxide and Tetramehylammonium Hydroxide" Journal of Photochemistry and Photobiology A: Chemistry 156 (2003) p. 219-225.*

(Continued)

*Primary Examiner* — Nathan Empie
(74) *Attorney, Agent, or Firm* — Brinks Hofer Gilson & Lione

(57) ABSTRACT

A method of manufacturing a ceramic coated fiber comprises heat treating an activated carbon coated fiber containing a ceramic precursor, to form a ceramic coated fiber.

18 Claims, 10 Drawing Sheets

U.S. PATENT DOCUMENTS

| | | |
|---|---|---|
| 4,178,413 A | 12/1979 | DeMunda |
| 4,256,607 A | 3/1981 | Yoshida et al. |
| 4,265,768 A | 5/1981 | Beasley et al. |
| 4,285,831 A | 8/1981 | Yoshida et al. |
| 4,312,956 A | 1/1982 | Chong et al. |
| 4,313,832 A | 2/1982 | Shimizu et al. |
| 4,321,154 A | 3/1982 | Ledru |
| 4,362,646 A | 12/1982 | Ikegami et al. |
| 4,476,191 A | 10/1984 | Girgis |
| 4,476,281 A | 10/1984 | Vaughn, Jr. |
| 4,513,032 A | 4/1985 | Klinkowski |
| 4,544,499 A | 10/1985 | Tran et al. |
| 4,550,015 A | 10/1985 | Korb et al. |
| 4,569,756 A | 2/1986 | Klein |
| 4,693,828 A | 9/1987 | Yoshioka et al. |
| 4,732,879 A | 3/1988 | Kalinowski et al. |
| 4,738,896 A | 4/1988 | Stevens |
| 4,740,540 A | 4/1988 | Kameda et al. |
| 4,760,046 A | 7/1988 | Burger et al. |
| 4,839,402 A | 6/1989 | Stevens |
| 4,917,835 A | 4/1990 | Lear et al. |
| 4,962,070 A | 10/1990 | Sullivan |
| 4,983,451 A | 1/1991 | Sugino et al. |
| 5,026,402 A | 6/1991 | Bose et al. |
| 5,039,635 A | 8/1991 | Stempin et al. |
| 5,039,651 A | 8/1991 | Kosaka et al. |
| 5,063,042 A | 11/1991 | Arita et al. |
| 5,102,855 A | 4/1992 | Greinke et al. |
| 5,114,887 A | 5/1992 | Sekine et al. |
| 5,143,756 A | 9/1992 | Cibulsky et al. |
| 5,162,286 A | 11/1992 | MacDowall |
| 5,185,037 A | 2/1993 | Kaijou |
| 5,204,310 A | 4/1993 | Tolles et al. |
| 5,204,376 A | 4/1993 | Henmi et al. |
| 5,206,207 A | 4/1993 | Tolles |
| 5,212,144 A | 5/1993 | Schwartz, Jr. |
| 5,250,491 A | 10/1993 | Yan |
| 5,276,000 A | 1/1994 | Matthews et al. |
| 5,277,802 A | 1/1994 | Goodwin |
| 5,304,527 A | 4/1994 | Dimitri |
| 5,318,846 A | 6/1994 | Bruening et al. |
| 5,320,089 A | 6/1994 | Schaefer et al. |
| 5,320,870 A | 6/1994 | Sorathia et al. |
| 5,328,758 A | 7/1994 | Markell et al. |
| 5,350,523 A | 9/1994 | Tomoi et al. |
| 5,376,407 A | 12/1994 | Feldman et al. |
| 5,389,325 A | 2/1995 | Bookbinder et al. |
| 5,416,056 A | 5/1995 | Baker |
| 5,424,042 A | 6/1995 | Mason et al. |
| 5,431,852 A | 7/1995 | Kaijou |
| 5,451,444 A | 9/1995 | DeLiso et al. |
| 5,482,915 A | 1/1996 | Golden et al. |
| 5,487,917 A | 1/1996 | Gadkaree |
| 5,501,801 A | 3/1996 | Zhang et al. |
| 5,512,351 A | 4/1996 | Miyamichi et al. |
| 5,538,929 A | 7/1996 | Sudhakar et al. |
| 5,540,759 A | 7/1996 | Golden et al. |
| 5,547,760 A | 8/1996 | Tarbet et al. |
| 5,580,770 A | 12/1996 | DeFilippi |
| 5,589,299 A | 12/1996 | Yamada et al. |
| 5,614,459 A | 3/1997 | Mondragon et al. |
| 5,616,532 A * | 4/1997 | Heller et al. ............. 502/242 |
| 5,618,766 A * | 4/1997 | Leiser et al. ............. 501/87 |
| 5,629,251 A | 5/1997 | Miyata |
| 5,707,471 A | 1/1998 | Petrak et al. |
| 5,710,092 A | 1/1998 | Baker |
| 5,759,942 A | 6/1998 | Tan et al. |
| 5,834,114 A * | 11/1998 | Economy et al. ............. 428/368 |
| 5,872,070 A | 2/1999 | Dismukes et al. |
| 5,965,483 A | 10/1999 | Baker et al. |
| 5,981,425 A * | 11/1999 | Taoda et al. ............. 502/208 |
| 5,997,829 A | 12/1999 | Sekine et al. |
| 6,036,726 A | 3/2000 | Yang et al. |
| 6,077,605 A | 6/2000 | McGowan et al. |
| 6,124,114 A | 9/2000 | Hoffman et al. |
| 6,130,175 A | 10/2000 | Rusch et al. |
| 6,177,373 B1 | 1/2001 | Sterte et al. |
| 6,283,029 B1 | 9/2001 | Tashiro et al. |
| 6,287,639 B1 * | 9/2001 | Schmidt et al. ............. 427/387 |
| 6,313,045 B1 | 11/2001 | Zhong et al. |
| 6,379,500 B2 | 4/2002 | Greenwood et al. |
| 6,508,962 B1 | 1/2003 | Economy et al. |
| 6,517,906 B1 | 2/2003 | Economy et al. |
| 6,638,885 B1 | 10/2003 | McGrath et al. |
| 6,680,277 B2 | 1/2004 | Morikawa et al. |
| 6,680,279 B2 | 1/2004 | Cai et al. |
| 6,706,361 B1 | 3/2004 | Economy et al. |
| 6,743,749 B2 * | 6/2004 | Morikawa et al. ............. 502/349 |
| 6,835,688 B2 | 12/2004 | Morikawa et al. |
| 6,872,317 B1 | 3/2005 | Nambu et al. |
| 6,878,666 B2 | 4/2005 | Domen et al. |
| 6,893,538 B2 | 5/2005 | Greenwood et al. |
| 6,905,772 B2 | 6/2005 | Shoup et al. |
| 7,211,513 B2 | 5/2007 | Remington et al. |
| 7,491,349 B2 | 2/2009 | Takahashi et al. |
| 2002/0006865 A1 | 1/2002 | Morikawa et al. |
| 2002/0074292 A1 | 6/2002 | Schlegel et al. |
| 2002/0151434 A1 | 10/2002 | Domen et al. |
| 2002/0169076 A1 | 11/2002 | Takeshi et al. |
| 2004/0024272 A1 * | 2/2004 | Cheung et al. ............. 585/261 |
| 2004/0058149 A1 | 3/2004 | Zhou et al. |
| 2004/0197552 A1 | 10/2004 | Maquin et al. |
| 2005/0164876 A1 | 7/2005 | Lee et al. |
| 2005/0202241 A1 | 9/2005 | Shang et al. |
| 2005/0221087 A1 | 10/2005 | Economy et al. |
| 2006/0014050 A1 | 1/2006 | Gueneau et al. |
| 2006/0078712 A1 | 4/2006 | Thierauf et al. |
| 2006/0099397 A1 | 5/2006 | Thierauf et al. |
| 2006/0264525 A1 | 11/2006 | Ohwaki et al. |

FOREIGN PATENT DOCUMENTS

| | | |
|---|---|---|
| EP | 0 036 584 A2 | 9/1981 |
| EP | 0 045 824 A1 | 2/1982 |
| EP | 0 285 321 A2 | 10/1988 |
| EP | 0 608 539 A1 | 8/1994 |
| EP | 0 630 685 A1 | 12/1994 |
| EP | 1 205 244 A1 | 5/2002 |
| FR | 2 827 856 A1 | 1/2003 |
| GB | 1 415 853 | 11/1975 |
| GB | 2 155 458 A | 9/1985 |
| JP | 56 0044039 A | 4/1981 |
| JP | 1-205103 | 8/1989 |
| JP | 2002321907 | 11/2009 |
| WO | WO 98/34723 | 8/1998 |
| WO | WO 99/61384 | 12/1999 |
| WO | WO 01/97973 | 12/2001 |
| WO | WO 03/010106 | 2/2003 |
| WO | WO 03/087002 | 10/2003 |
| WO | WO 2005/087679 | 9/2005 |

OTHER PUBLICATIONS

Jouyban et al "Mathematical Representation of Solute Solubility in Supercritical Carbon Dioxide Using Empirical Expression" Journal of Supercritical Fluids 24 (2002) p. 19-35.*

Wakayama et al "Nanoporous Titania Synthesized by a Nanoscale Casting Process in Supercritical Carbon Dioxide" J. Am. Ceram. Soc. 85 [1] (2002) p. 161-164.*

Caruso et al Porous "Coral-like" TiO2 Structures Produced by Templating Polymer Gels, Langmuir, vol. 14, No. 22, 1998 p. 6333-6336.*

"Ion Exchange", Kirk-Othmer Encyclopedia of Chemical Technology, 3$^{rd}$ Ed., vol. 13, pp. 685-689 and 694, 1981.

Abstract for "Carborundum Process Converts Pitch Into Non-Flammable Fiber", Industrial Research vol. IR-100, Circle 231, 1 page, 1972.

Ahmadpour, et al., "The Preparation of Active Carbons from Coal by Chemical and Physical Activation", Carbon, vol. 34, No. 4, pp. 471-479, 1996.

Andreopoulos, et al., "Thermally Activated Phenolic Fibers", Chemistry of Materials, vol. 3, No. 4, pp. 594-597, 1991.

Asahi, R., et al., "Visible-light photocatalysis in nitrogen-doped titanium oxides", Science, vol. 293,: 269-271, 2001.

Ayles, "Phenolic", Modern Plastics Encyclopedia Handbook, pp. 78-80, 1994.

Carrott, et al., "Preparation of activated carbon 'membranes' by physical and chemical activation of cork", Carbon, vol. 37, pp. 515-517, 1999.

International Search Report and Written Opinion for PCT/US2005/008008, 12 pages, Date of Mailing Jul. 22, 2005.

Dimotakis, et al., "Water Vapor Adsorption on Chemically Treated Activated Carbon Cloths", Chemistry of Materials, vol. 7, pp. 2269-2272, 1995.

Dominguez, et al., "Design of High Efficiency Polymeric Cation Exchange Fibers", Polym. Adv. Techol. 12, pp. 197-205, 2001.

"Ion Exchangers", Dorfner, editor, pp. 28-45 and 206-285, 1990.

Economy, et al, "Adsorption Characteristics of Activated Carbon Fibers", Applied Polymer Symposium No. 29, 199-211, 1976.

Economy, et al., "Tailoring Carbon Fibers for Adsorbing Volatiles", Chemtech, pp. 597-603, 1992.

Economy, "Now that's an interesting way to make a fiber!", Chemtech, vol. 10, pp. 240-247, 1980.

Economy, et al., "Polymeric Ion-Exchange Fibers", Ind. Eng. Chem. Res., 41, pp. 6436-6442, 2002.

Ermanlenko, et al., "Chemically Modified Carbon Fibers and Their Applications", VCH Publishers, pp. 59-73, 1990.

Feng, et al., "Functionalized Monolayers on Ordered Mesoporous Supports", Science, vol. 276, pp. 923-926, 1997.

Foster, et al., "Adsorption Characteristics of Trace Volatile Organic Compounds in Gas Streams onto Activated Carbon Fibers", Chemistry of Materials, vol. 4, pp. 1068-1073, 1992.

Grynszpan, et al., "Synthesis and reactions of large-ring spirodienone calixarene derivatives", Pure & Appl. Chem., vol. 68, No. 6, pp. 1249-1254, 1996.

Ihara, et al. "Visible-light-active titanium oxide photocatalyst realized by an oxygen-deficient structure and by nitrogen doping.", Applied Catalysis B: Environmental, 42, pp. 403-409, 2003.

Jagtoyen, et al., "Some Considerations of the Origins of Porosity in Carbons from Chemically Activated Wood", Carbon, vol. 31, No. 7, pp. 1185-1192, 1993.

Kim, et al., "Preparation of $TiO_2$ Fiber and its Photocatalytic Properties", Materials Science Forum, vol. 439, pp. 271-276, 2003.

Kunin, "Six Decades of Ion Exchange Technology at Rohm and Haas", Chemical Heritage 17:2, pp. 8, 9, 36-38, 1999.

Lee, et al., "Vapor adsorption on coal-and wood-based chemically activated carbons (II) adsorption of organic vapors", Carbon, vol. 37, pp. 15-20, 1999.

Lin, et al., "Extraction of Gold from Au(III) Ion Containing Solution by a Reactive Fiber", Journal of Applied Polymer Science, vol. 49, pp. 1635-1638, 1993.

Lin, et al., "Studies of the Preparation, Structure, and Properties of an Acrylic Chelating Fiber Containing Amidoxime Groups," Journal of Applied Polymer Science, vol. 47, pp. 45-52, 1993.

Lin, et al., "The Preparation and Properties of Activated Carbon Fibers Derived from Phenolic Precursor", Applied Polymer Symposium, No. 21, pp. 143-152, 1973.

Liu, et al., "Surfactant-Directed Synthesis of Nanoporous Thiol-Functionalized Organic-Inorganic Hybrid Fibers for Highly Selective Removal of Mercury", Polymeric Materials: Science & Engineering, 91, pp. 1037-1038, 2004.

Liu, et al., "Novel Polymeric Chelating Fibers for Selective Removal of Mercury and Cesium from Water", Environmental Science and Technology, vol. 37, No. 18, pp. 4261-4268, 2003.

"Glass fibers chelate heavy metals", Chemical & Engineering News, vol. 81, No. 37, p. 21, 2003.

Liu, et al., "Hybrid Mesoporous Materials with Functionalized Monolayers", Chem. Eng. Technol., 21, pp. 97-100, 1998.

Liu, et al., "Hybrid Mesoporous Materials with Functionalized Monolayers", Adv. Mater., vol. 10, No. 2, pp. 161-165, 1998.

Mercier, et al., "Heavy Metal Ion Adsorbents Formed by the Grafting of a Thiol Functionality to Mesoporous Silica Molecular Sieves: Factors Affecting Hg(II) Uptake", Environ. Sci. Technol., vol. 32, No. 18, pp. 2749-2754, 1998.

Molina-Sabio, et al., "Development of Porosity in Combined Phosphoric Acid-Carbon Dioxide Activation", Carbon, vol. 34, No. 4, pp. 457-462, 1996.

Molina-Sabio, et al., "Porosity in Granular Carbons Activated with Phosphoric Acid", Carbon, vol. 33, No. 8, pp. 1105-1113, 1995.

Nam, K., et al., "Preparation and characterization of $TiO_2$ fiber and its photocatalytic properties", Paper # 291, Department of Chemical Engineering, Yonsei University, Seodaemun 134, Seoul, Korea, Sep. 19, 2002.

Odian, Principles of Polymerization, Third Edition John Wiley & Sons, pp. 125-132, 1991.

Przepiorski, et al., "Activated carbons containing $TiO_2$: characterization and influence of a preparation method on the state of $TiO_2$ supported", Journal of Materials Science, 36, pp. 4249-4257, 2001.

Rodriguez, "Table 15.11 Aldehyde condensation products", Principles of Polymer Systems, Fourth Edition, p. 638, 1996.

Sato, "Photocatalytic activity of $NO_x$-doped $TiO_2$ in the visible light region", Chemical Physics Letters, 123, No. 1,2, pp. 126-128, 1986.

Search Report for Patent Cooperation Treaty application No. PCT/US 01/41081, 7 pages, Date of Mailing Nov. 9, 2001.

Search Report for Patent Cooperation Treaty application No. PCT/US 01/19952, 8 pages, Date of Mailing Nov. 14, 2001.

Search Report for Patent Cooperation Treaty application No. PCT/US 01/19946, 8 pages, Date of Mailing Nov. 14, 2001.

Solum, et al., "Evolution of Carbon Structure in Chemically Activated Wood", Carbon. vol. 33, No. 9. pp. 1247-1254, 1995.

Tamai, et al., "Simple preparation of $TiO_2$ particles dispersed activated carbons and their photo-sterilization activity", Journal of Materials Science, 37, pp. 3175-3180, 2002.

Toles, et al., "Production of Activated Carbons from a Washington Lignite Using Phosphoric Acid Activation", Carbon, vol. 34, No. 11, pp. 1419-1426, 1996.

Molina-Sabio, et al., "Influence of the atmosphere used in the carbonization of phosphoric acid impregnated peach stones", Carbon, vol. 33, No. 8, pp. 1180-1182, 1995.

* cited by examiner

HIGH SURFACE AREA CERAMIC COATED FIBERS

CROSS REFERENCE TO RELATED APPLICATION

This application is a continuation application of U.S. application Ser. No. 10/797,582, filed Mar. 10, 2004 now abandoned, the entire contents of which are hereby incorporated by reference.

FEDERALLY SPONSORED RESEARCH OR DEVELOPMENT

This invention was made with government support under Contract Number CTS0120978 awarded by the National Science Foundation (NSF). The Government has certain rights in this invention.

BACKGROUND

More than 700 organic compounds have been identified in sources of drinking water in the United States (Stachka and Pontius, 1984) and elsewhere. Many water utilities, companies and government agencies must remove or destroy organic compounds from polluted groundwater supplies before those groundwater supplies can be used as drinking water. Additionally, many drinking water utilities are faced with the formation of disinfection by-products in finished water. Disinfection by-products are compounds formed in the water treatment process as a result of the disinfection process. In this process, a disinfectant such as chlorine is added to source water, where it reacts with a portion of the background organic matter (BOM) present in the source water to produce disinfection by-products. The reactive portions of the BOM are referred to as disinfection by-product precursors.

Considerable research is being directed at effective and economical treatment strategies that minimize the production of disinfection by-products. Advanced oxidation processes (AOPs) are alternative processes which destroy organic compounds and turn them into nontoxic forms, such as carbon dioxide and water. AOPs involve the generation of highly reactive radicals, such as the hydroxyl radical (OH.), which are responsible for the destruction of the organic compounds. AOPs can be classified into two major groups: AOPs involving homogeneous reactions using hydrogen peroxide ($H_2O_2$), ozone ($O_3$), chlorine, and ultraviolet (UV) light, alone or in combination; and AOPs employing heterogeneous reactions using photoactive catalysts, such as semiconductors like titanium dioxide ($TiO_2$) and nitrogen-doped titanium dioxide ($TiO_{2-x}N_x$). In the latter case—the photocatalytic oxidation processes—photoactive semiconductor catalysts are immersed in an oxygenated aqueous solution and illuminated with UV or visible radiation, so that reactive oxygen species are produced, causing the oxidation of organic compounds.

The primary oxidant responsible for the photocatalytic oxidation of organic compounds in aqueous solutions is believed to be the highly reactive hydroxyl radical (OH.), although direct reactions of adsorbed organic compounds with surface species, such as holes, have also been reported (Völz et al., 1981; Ceresa et al., Matthews, 1984; and Turchi and 011 is, 1990). When a photoactive semiconductor is illuminated with photons of the band gap energy of the semiconductor, or greater, photons excite electrons from the valence band, overcoming the energy of the band gap to the conduction band, and leaves electron vacancies, or holes, in the valence band. For example, the anatase form of $TiO_2$ has a band-gap energy of about 3.2 eV, which is equivalent to the energy of UV light with a wavelength of 387 nm. Consequently, the anatase form of $TiO_2$ can be activated by radiation with wavelengths less than 387 nm. The excited electrons and the resulting holes may take part in redox processes with adsorbed species, such as $H_2O$, $OH^-$, organic compounds and $O_2$ at the water-solid interface. The holes may take part in oxidation half reactions with adsorbed $H_2O$ or $OH^-$ to form hydroxyl radicals. The electrons take part in the reduction half reactions with adsorbed $O_2$ to produce the superoxide radical $O_2^-$, which may also in turn produce $H_2O_2$ and OH. (Okamoto et al., 1985).

For high photocatalytic efficiency, mesoporous $TiO_2$ with its large surface area is highly desirable, and it was first prepared using a phosphate surfactant through a modified sol-gel process. The product was not pure $TiO_2$ because of significant amounts of residual phosphorus, and its mesoporous structure underwent partial collapse during template removal by calcination. Another approach produced mesoporous $TiO_2$ from amphiphilic poly(alkylene) block copolymers as structure-directing agents and organic titanium salts as precursors in a non-aqueous solution. Slight changes in reaction conditions, however, often produced very different results, rendering this method difficult to reproduce. A third method, using dodecylamine as a directing agent and titanium isopropoxide as the precursor, and emptying the pores by extractions, yielded a porous structure that was not retained after heat treatment in dry air at 300° C. Thus, it has so far been difficult to produce the highly crystalline $TiO_2$ that is required for photocatalysis.

A second issue of current $TiO_2$ photocatalysis technology is the requirement of ultraviolet light for activation. Because of the large energy of the band gap of $TiO_2$ (Eg=3.2 eV in anatase), its use as a photocatalyst is limited to radiation with a wavelength of less than 380 nm. A material catalytically active when exposed to visible light of wavelengths longer than 380 nm would allow for satisfactory photocatalysis in environments where less intense light is available, for instance indoors or in a vehicle.

A further major issue of the current technology is that the powder form of the photocatalyst is difficult to handle, and too fine to be recovered from photoreactors. Thus, several films of $TiO_2$ on various substrates and supports have been developed for photocatalytic applications. However, particle sintering and agglomeration greatly reduce the surface area of the photocatalyst.

The bonding of the $TiO_2$ to the substrate is also a source of problems. Films of $TiO_2$ have been assembled on substrates by direct growth and post synthetic crystal attachment. Both methods rely on chemical binders to immobilize $TiO_2$ to the substrate surface. Unfortunately, organic binders are susceptible to decomposition under UV light. Consequently, the $TiO_2$ films become loose from the substrate, and are easily detached.

Powders, fibers and films of $TiO_2$ have been reported, and a number of photocatalytic $TiO_2$ powder preparations are commercially available. However, these powders are difficult to apply to water purification, and the surface area of the powders is low, resulting in low catalytic activity and only a small number of catalytic sites.

In contrast, $TiO_2$ fibers have a very high surface area, high wear and mechanical strength, and high thermal stability. Moreover, when used in chemical reactors, $TiO_2$ fibers cause only a small pressure drop and can serve as a reinforcement material and as a matrix of various shapes and sizes.

$TiO_2$ fibers may be prepared by various fabrication methods. For example, $TiO_2$ fibers were prepared by solvothermal reaction of a fibrous $K_2Ti_4O_9$ precursor, by ion-exchange reaction of $K_2O.4TiO_7$ fibers and thermal decomposition of $H_2Ti_4O_9$.

Activated carbon fibers (ACF) are traditionally produced by heating an organic precursor until carbonized, and then activating the carbonized material. Activation is achieved typically by heating the carbonized material in an oxidizing environment. Alternatively, the carbon may be activated chemically. This process involves impregnating the carbon precursor with, for example, phosphoric acid, zinc chloride, or potassium hydroxide, followed by carbonization.

The above methods, however, yields brittle and frangible ACF, limiting their use to systems containing some mechanical support. This problem has been mitigated by preparing fibers where activated carbon is formed as a coating on substrate fibers.

For example, U.S. Pat. No. 5,834,114 describes glass or mineral fibers coated with activated carbon. These are prepared by coating the fiber substrate with a resin, cross-linking the resin, heating the coated fiber substrate and resin to carbonize the resin, and exposing the coated fiber substrate to an etchant to activate the coated fiber substrate.

U.S. Pat. No. 6,517,906 describes coating the substrate fibers with a mixture containing an organic polymeric material, and a chemical activating agent, for example a Lewis acid or base. This mixture carbonizes at temperatures lower than those required by earlier methods, allowing for the formation of activated carbon coatings on low melting point fibers, such as HEPA fibers.

SUMMARY

In a first aspect, the present invention is a method of manufacturing a ceramic coated fiber, comprising heat treating an activated carbon coated fiber containing a ceramic precursor, to form a ceramic coated fiber.

In a second aspect, the present invention is a ceramic coated fiber, comprising (a) a fiber, and (b) ceramic, coated on the fiber. The ceramic has a BET surface area of at least 60 $m^2/g$, and the ceramic comprises crystalline ceramic.

In a third aspect, the present invention is a method for manufacturing an intermediate for the fabrication of ceramic coated fibers, comprising heating an activated carbon coated fiber containing a ceramic precursor, to cure the precursor.

In a fourth aspect, the present invention is a ceramic coated fiber comprising (a) a fiber, and (b) ceramic, coated on the fiber. The ceramic has a BET surface area of at least 50 $m^2/g$, and the ceramic comprises at least one member selected from the group consisting of $Al_2O_3$, $ZrO_2$, and MgO.

DETAILED DESCRIPTION

Figure 1:
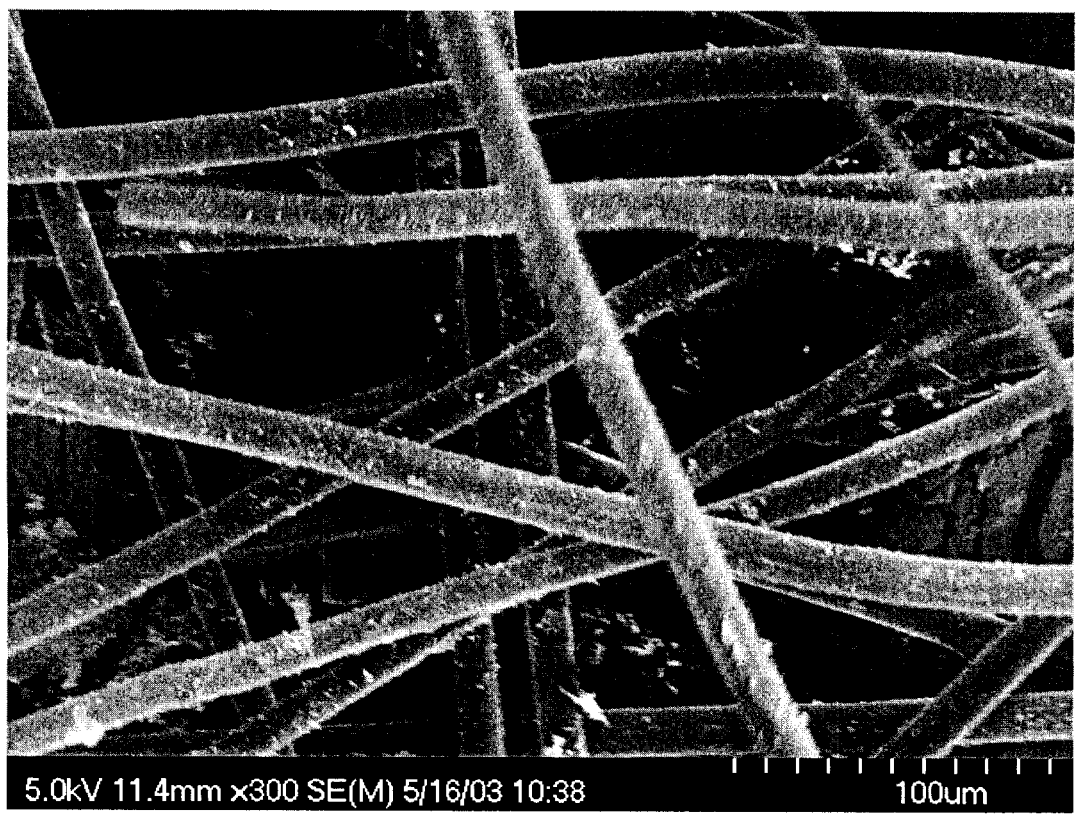
FIG. 1 illustrates a scanning electron micrograph (SEM) of ceramic fibers produced according to the method of Example 1.

Activated carbon does not resist temperatures higher than 573 K in an oxidative atmosphere. Therefore, it had been thought to be inapplicable to use activated carbon as a substrate fiber for fabrication processes requiring high temperature calcination, such as the manufacturing of ceramic coated fibers. The present invention is based on the discovery that, despite this instability at high temperatures, activated carbon can be used as a template in the formation of ceramic coated fibers.

Activated carbon coated fibers are first prepared by coating substrate fibers with activated carbon or an activated organic coating as described in U.S. Pat. No. 6,517,906. Example substrate fibers include HEPA filters, synthetic fibers used in clothing, polyesters, polyethylene, polyethylene terephthalate, nylon 6, nylon 66, polypropylene, KEVLAR™, TEFLON™, liquid crystalline polyesters, and syndiotactic polystyrene. Glass fibers such as e-glass fibers; mineral fibers such as asbestos and basalt; ceramic fibers such as $TiO_2$, SiC, and BN; metal fibers (or wires) such as iron, nickel, gold, silver, aluminum and platinum; polymer fibers such as TYVEK™; and combinations thereof. Some preferred substrate fibers are listed in the table below.

| Company | Product Line | Description |
|---|---|---|
| CRANE & CO. | Crane 230 (6.5 µm) | Non-woven Fiber Glass Mats |
| | Crane 232 (7.5 µm) | Non-woven Fiber Glass Mats |
| FIBRE GLAST | 519 (0.75 oz.) | wovens |
| | 573 (9 oz.) | wovens |
| HOLLINGSWORTH & VOSE | BG05095 | glass paper or felts |
| | HE1021 | |
| JOHNS MANVILLE | 7529 (11 µm) | non-woven fiber glass mats |
| LYDALL MANNING | MANNIGLAS(R) | non-woven fiber glass mats |
| DUPONT | TYVEK(R) | HDPE Spun bonded paper |

The substrate fibers may be present in any form. Examples include loose fibers, woven and non-woven fabrics, papers, felts and mats. The substrate fibers may be made from substrate fibers already present in a specific form, or the substrate fibers may first be prepared from loose substrate fibers, and made into the specific form. The length of the substrate fibers is not limited, and may be, for example, 0.01 mm to over 100 m in length, but preferably at least 3 micrometers. The substrate fibers may be prepared from longer substrate fibers, then cut or chopped. Furthermore, the diameter of the substrate fibers is also not limited, and may be, for example 100 Å to 1 mm in diameter. Preferably, the fibers have an aspect ratio of at least 10.

If the substrate fibers are susceptible to oxidation, it may be advantageous to coat them with an oxidation resistant coating, before forming the activated carbon on the fibers. Examples of oxidation resistant coating include water glass and phosphate glass.

The activated carbon coated fibers are infiltrated with ceramic precursors by immersion in a solution of one or more ceramic precursors in a volatile solvent. In general, ceramic precursors are compounds of one or more elements present in the ceramic and volatile components, such as halides, nitrates, nitrides, nitrates, hydroxides, organic acid salts and organometallic complexes. When subjected to high temperature treatment, the ceramic elements and any oxygen are left as a ceramic deposit, whereas the remainder of the precursor is volatilized.

Ceramic precursors are soluble compounds of the first group, second group, third group, fourth group, the transition metals, the lanthanide and actinide elements, N, O, Se, Te, and Po. Example ceramic precursors include $Ti(t-BuO)_4$, $Ti(i-Pro)_4$, $Si(OEt)_4$, $ZnCl_2$, $ZrOCl_2$, $ZrO(OH)Cl$, $Zr(COOCH_3)_4$, $MgCl_2$, $Mg(COOCH_3)_2$, and $MgSO_4$. A mixture of two or more precursors may be used, for instance if a secondary, ternary or quaternary ceramic compound is desired. An oxynitride ceramic coating may be obtained by adding a nitrogen dopant such as a tetraalkylamonium salt. Likewise, an oxysulfide coating may be made by adding a sulfur dopant such as thiourea.

The excess precursor is removed, and the infiltrated precursor may be hydrolyzed by exposure to the moisture in the air, yielding a composite of carbon and the precursor or the hydrolyzed precursor.

The ceramic precursor should preferably accumulate in the pores of the template to form an interconnected solid or gel. The system is then subjected to a heat treatment, which may remove residual solvent, cure the precursor, as well as remove the activated carbon, and crystallize the ceramic. For example, the heat treatment may include a first heating at 250° C. to 600° C., or 250° C. to 400° C., optionally in an inert atmosphere, to remove residual solvents and to cure the ceramic precursor. A second heating may follow, for example at 400° C. to 1000° C., in an oxidizing atmosphere, removing the carbon substrate and crystallizing the ceramic, and if necessary, oxidizing the cured precursor. The carbon substrate may also be oxidized by irradiation of the fibers, or by treatment with chemical oxidizers.

The resulting fibers may be further modified by adding one or more additional precursors, for example $AgNO_3$ or $Pd(acac)_2$, followed by additional rounds of heating. Such heating may be carried out in a reducing atmosphere, such as an atmosphere containing $H_2$.

For example, activated carbon coated fibers may be used to prepare $Al_2O_3$ coated fibers. To this end, ACF may be impregnated in an aqueous solution of $AlCl_3$, dried, and heat-treated under $N_2$ at a temperature of usually 500° C. to 700° C. A second heat treatment, this time in an oxidizing atmosphere, removes the carbon. The material is then calcined, yielding thermally stable $Al_2O_3$ coated fibers.

When the temperature of the second heat treatment is about 500° C. or above, air is preferred as an oxidizing atmosphere, as opposed to pure $O_2$. For lower temperatures, such as 450° C., pure $O_2$ is preferable. In general, lower temperatures require longer heating times for the complete removal of the carbon template. For instance, at 500° C., it usually takes more than 24 hours to burn off the template, whereas only a few seconds of heating are needed at 900° C. Lower temperatures also yields $Al_2O_3$ coated fibers with a higher Brunauer-Emmett-Teller (BET) surface area and a poorly crystalline structure. By contrast, higher temperature yields fibers with a lower BET surface area and the ceramic is more crystalline.

The ceramic coating may be present on isolated regions on the surface of the substrate fibers, may completely enclose the substrate fibers, or enclose all of the substrate fibers except the ends of the substrate fibers. For example, if the substrate fibers were completely enclosed by the ceramic coating, then chopping would result in the ends of the fibers being exposed.

The weight ratio between the ceramic coating and the substrate fibers in the ceramic coated product fibers is not limited, but does affect final properties. For example, if the amount of the ceramic coating is very large compared to the amount of substrate fibers, then the brittleness of the ceramic coating may reduce the flexibility of the product ceramic coated fibers. Preferably, the product ceramic coated fibers include 10 to 90% by weight of the nanoporous organosilica ceramic coating, more preferably 20 to 80% by weight of the ceramic coating, including 30%, 40%, 50%, 60%, and 70% by weight of the ceramic coating.

Ceramic coated fibers may have BET surface areas of at least 50 $m^2/g$, preferably more than 50 $m^2/g$, more preferably at least 60 $m^2/g$, including 60-2000 $m^2/g$, and 100-500 $m^2/g$. Preferably, the ceramic of the ceramic coated fibers contains crystalline ceramic, and may also include an amorphous phase. The crystallites (or particles) of ceramic preferably have an average particle diameter of 2 nm to 50 nm. Even though the temperatures used to form the ceramic coated fibers may appear insufficient for crystallization of the bulk ceramic, crystalline material is present. One possible explanation is that the activated carbon catalyzes the crystallization of the ceramic. Furthermore, the coating holds to the fiber without the need for any binders.

The ceramic coated fibers of the invention may be used to catalyze photochemical reactions, for example for the photo-degradation of unwanted organic and biological compounds or the disinfection of bacteria. Thus, the fibers may be used for the purification and sterilization of water and air, or for the disinfection of tools such as medical room utensils. Other uses include substrates for catalytic material (for example, platinum), and abrasive materials. The fibers of the invention may also be manufactured with conductive fibers, such as metal fibers. Thus, product fibers with a metal core and a catalytic oxide surface may be formed, and use as sensors, for instance as oxygen sensors to monitor combustion.

EXAMPLES (1) $TiO_2$ Fibers

A carbon template was prepared by coating glass fibers with PAN resin prior to activation. After activation with $H_2O$, the surface area of carbon was 1800 $m^2/g$ and the pore size was from 1 nm to 10 nm. The pore system of the carbon template was then infiltrated with titanium tetraisopropoxide (TTIP) by wet impregnation for 24 hours at room temperature (20-22° C.). After removing the excess TTIP by washing with ethanol, precursor hydrolysis was initiated by expoure to air moisture. Mesoporous inorganic particles were then obtained by crystallization or polymerization of $TiO_2$ at 250-400° C. in a nitrogen atmosphere for 4 hours, followed by removal of the carbon in air at the heating rate of 1° C./min. The surface area of the final product fibers was 500 $m^2/g$, based on the $TiO_2$ weight.

FIG. 1 illustrates a scanninq electron micrograph (SEM) of the product fibers.

(2) $TiO_2$ Fibers

An activated carbon coated fiber was made by coating glass fiber with phenolic resin prior to activation. Following activation with $N_2$, the surface area of the carbon was about 1200 $m^2/g$, and the pore size was from 1 to 3 nm. The pore system of the activated carbon coated fiber was infiltrated with the titanium n-butoxide by wet impregnation for 24 h at room temperature. After removal of excess n-butoxide by ethanol wash, the hydrolysis of precursor was initiated by exposure to air moisture. Mesoporous inorganic particles, with an average particle diameter from about 2 nm to about 50 nm, were then obtained by crystallization or polymerization of $TiO_2$ at 300° C. in air for 4 hours, followed by removal of the carbon at 550° C. in air for 2 hours. The surface area was 230 $m^2/g$ based on the $TiO_2$ weight.

(3) TiON Fibers

The activated carbon coated fiber was made by coating glass fibers with PAN resin prior to activation. After activation with $H_2O$, the surface area of the carbon was about 1800 $m^2/g$, and the pore size was about 1 nm. The pore system of activated carbon coated fiber was infiltrated with a 100:2 mixture of titanium tetroisopropoxide and a nitrogen dopant tetramethylammonium salt by wet impregnation for 24 h at room temperature. The surface was washed with ethanol, and the hydrolysis of the precursor was initiated by exposure to air moisture. The mesoporous inorganic spheres were then obtained by crystallization or polymerization of the TiON at 300° C. in air for 1 h, followed by removal of the carbon and of the nitrogen dopant at 500° C. in air for 3 h.

(4) TiOS Fibers

Two grams of thiourea were dissolved in 20 g of N,N-dimethylformamide (DMF) and added to 10 g TTIP, and 2 g of ethanol were added to the mixture to obtain a transparent solution. The activated carbon coated fiber was made by coating glass fiber with PAN or phenolic resin prior to activation. After activation with $H_2O$, the surface area of carbon was about 1800 $m^2/g$ and the pore size was about 1 nm. The pore system of the activated carbon coated fiber was infiltrated with the above-described solution by wet impregnation for 24 hours at room temperature. The carbon surface was washed with acetone, and the hydrolysis of the precursor was initiated by exposure to air moisture. The mesoporous inorganic spheres were then obtained by crystallization or polymerization of TiOS at 500° C. in air for 3 hours, followed by removal of the carbon and of the sulfur dopant at 500° C. in air for 1 hours.

(5) Ag—TiON Fibers

TION fibers prepared according to the method of Example (3) were immersed in a 10% (wt) silver nitrate solution for 12 hours at room temperature. The fibers were then washed with de-ionized (DI) water and heated at 300° C. for 2 hours.

(6) Pd—TiON Fibers

TiON fibers prepard according to the method of Example (3) were immersed in a 1% (wt) $Pd(acac)_2$ toluene solution for 12 hours at room temperature. The fibers were then heated at 400° C. for 1 hour and reduced in $H_2$ at 200° C. for 3 hours.

(7) Photodegradation with $TiO_2$ Fibers and 254 nm Light

Figure 2A:
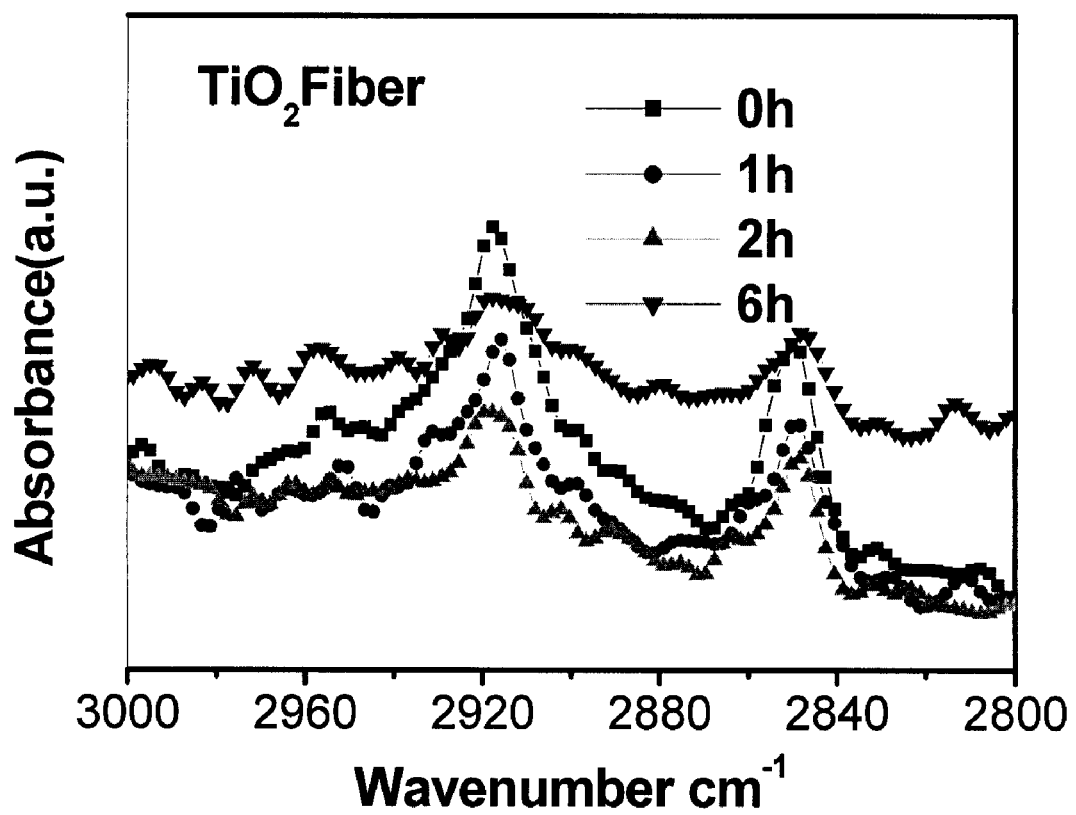
FIG. 2 illustrates the photodegradation of stearic acid catalyzed by the fibers of Example 1 (FIG. 2A), and by a reference commercial $TiO_2$ photocatalyst (FIG. 2B).
Figure 2B:
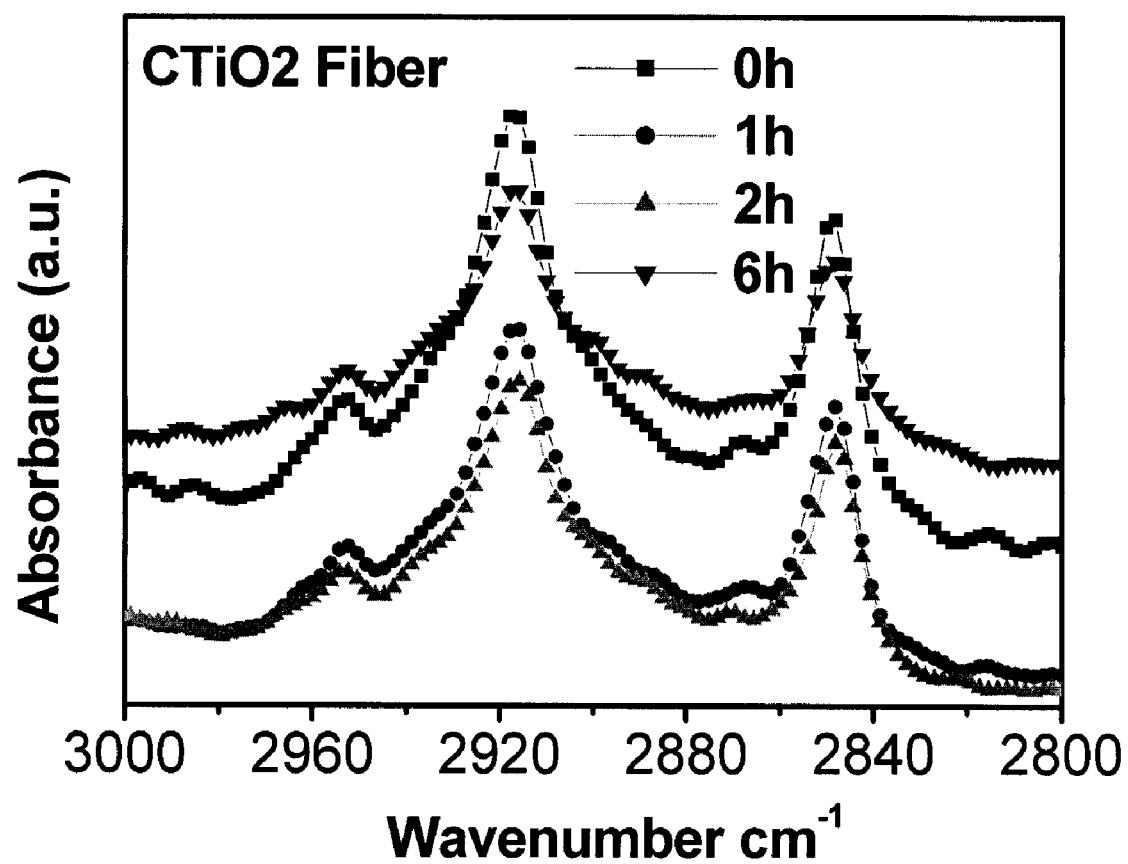

The photodegradation rate of stearic acid is commonly used to assay the photocatalytic activity of semdiconductor films. Accordingly, stearic acid was deposited on a 10 mm×10 mm fiber sample by dip coating the fiber in a methanolic solution of stearic acid 0.02 M. The photocatalytic activity was compared to that of a reference photocatalyst film obtained by deposition of commercial $TiO_2$ (Hombikat UV 100) slurry via dip coating followed by washing in distilled water and drying in air for 1 hour at 80° C. The degradation rates of stearic acid were calculated by measuring the integrated absorbance of stearic acid between 2700 and 3000 $cm^{-1}$ in the infrared spectrum. After a 2 hours-long exposure to a light source of 254 nm wavelength and 2.8 $mW/cm^2$ intensity, the percentage of degraded stearic acid was 39% for the mesoporous $TiO_2$ fibers of the invention, as illustrated in FIG. 2A, and 27% for the reference photocatalyst, as illustreated in FIG. 2B.

(8) Photodegradation with $TiO_2$ Fibers and 365 nm Light

Figure 3A:
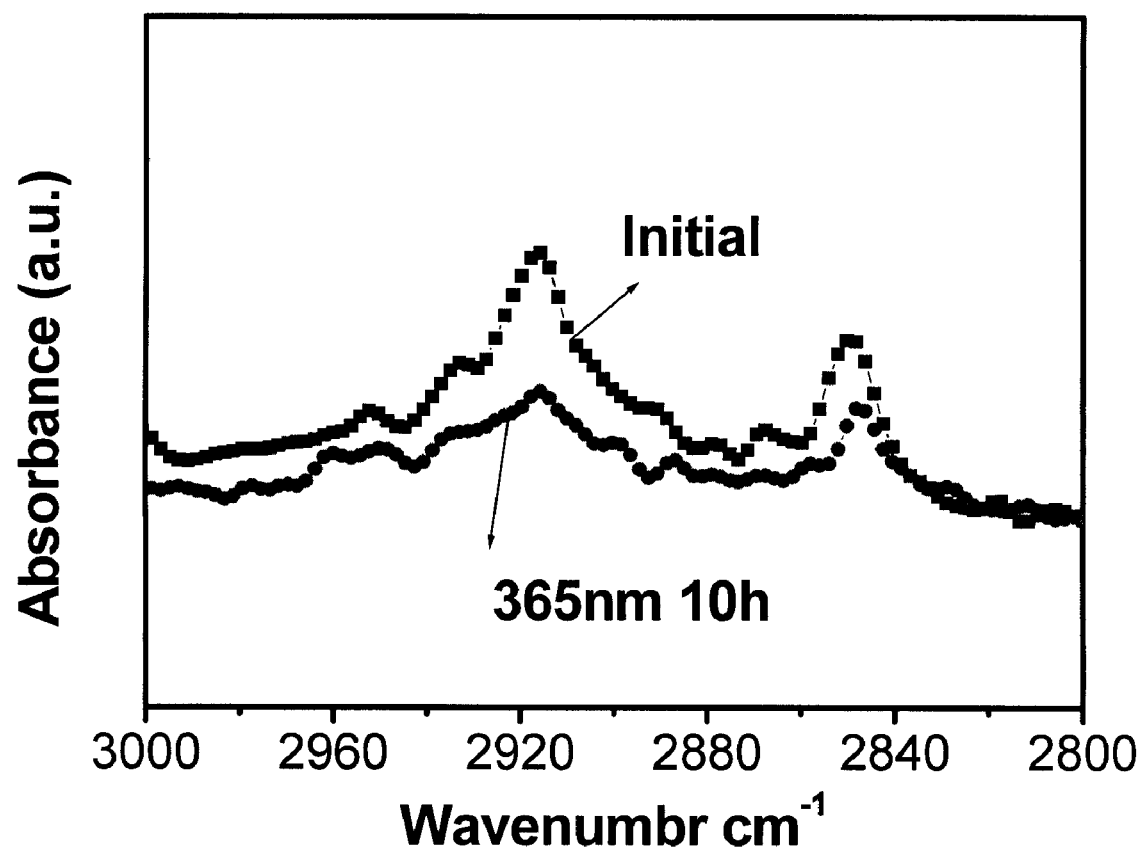
FIG. 3 illustrates the photodegradation of stearic acid catalyzed by the fibers of Example 1 (FIG. 3A), and by a reference commercial $TiO_2$ photocatalyst (FIG. 3B).
Figure 3B:
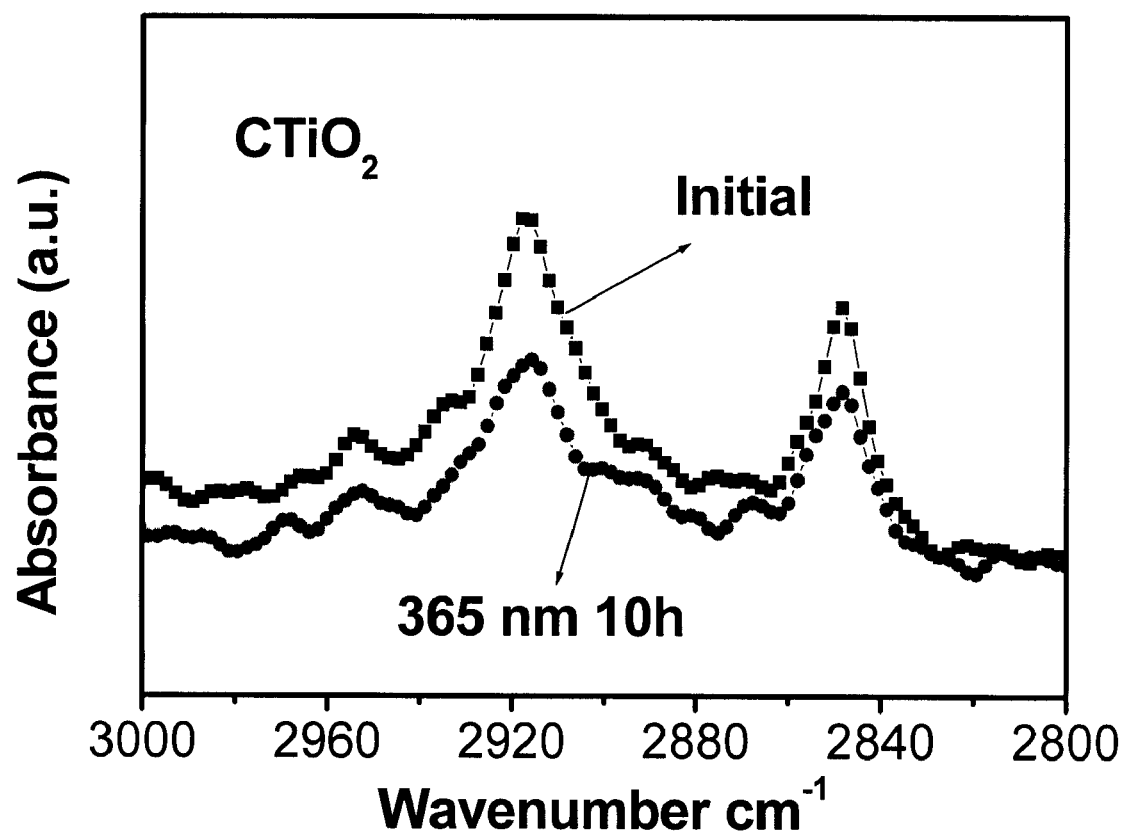

The procedure of Example (7) was followed, with a 12 hours-long exposure to a light source of 365 nm wavelength and 2.4 $mW/cm^2$ intensity. The percentage of degraded stearic acid was 73% for the mesoporous $TiO_2$ fibers of the invention, as illustrated in FIG. 3A, and 42% for the reference photocatalyst, as illustrated in FIG. 3B.

(9) Photodegradation of Humic Acid with TiON Fibers

Figure 4:
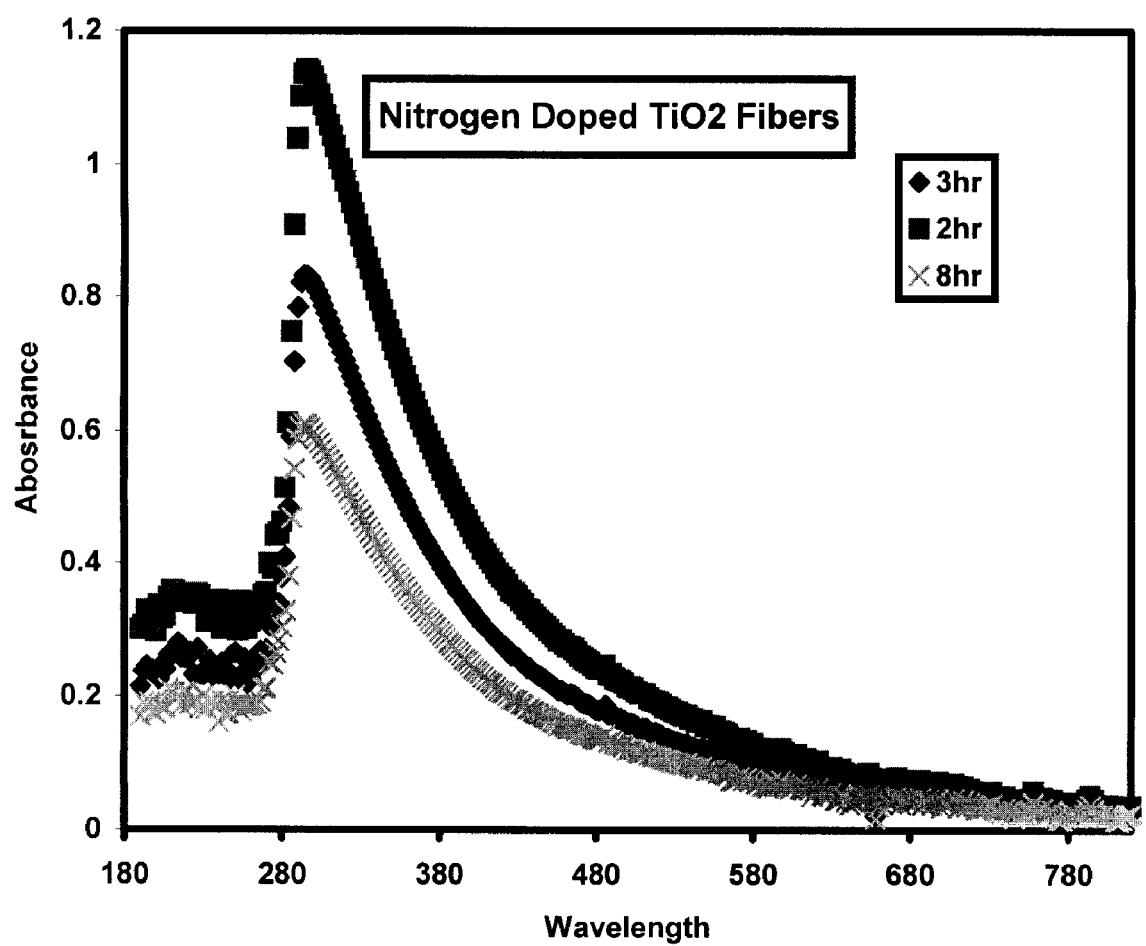
FIG. 4 illustrates the photodegradation of humic acid catalyzed by the TiON fibers of Example (3).

Humic acid was deposited on a 10 mm×10 mm sample of the TiON fibers of Example (3) by dip coating in a 0.25% (wt) aqueous humic acid solution. A degradation experiment according to the procedure of Example (7) was then conducted under a visible light source with an intensity of 1.9 $mW/cm^2$. The degradation of the humic acid was calculated by monitoring the absorption intensity of the humic acid solution at 400 nm in a UV-Vis spectrophotometer. As illustrated in FIG. 4, after 8 hours of exposure to the light source, the TiON fiber of the invention had degraded 43% of the humic acid, whereas the reference photocatalyst of Example (7) showed no photocatalytic activity whatsoever.

(10) Disinfection of Bacterial Cultures

Figure 5:
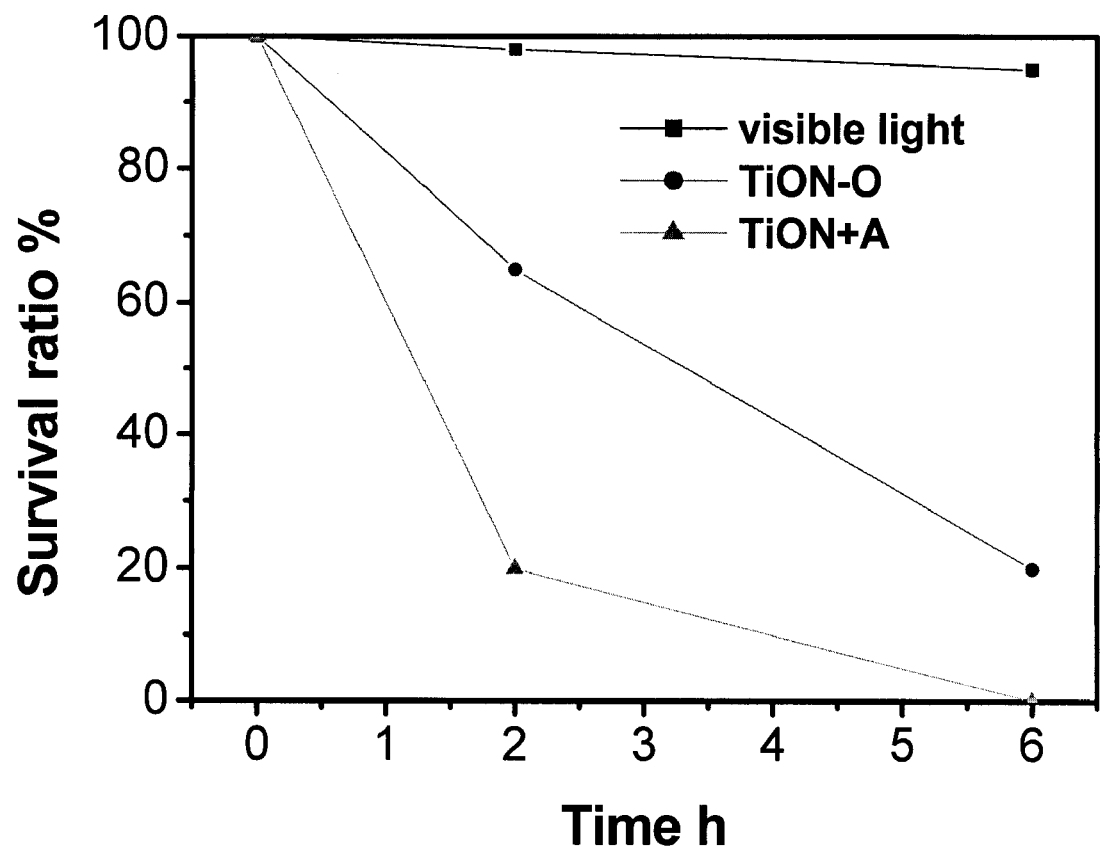
FIG. 5 illustrates the incubation of an *E. coli* bacterial culture with the TiON fibers of Example (3) and with the Ag—TiON fibers of Example (5).

A culture of *E. coli* bacteria was grown aerobically in a test-tube at 37° C. for 18 hours. The TiON fibers of Example (3) and the Ag—TiON fibers of Example (5) were then tested as disinfectants on this culture by incubation under visible light at room temperature for 5 hours. Following the incubation, the number of viable cells in the disinfected samples and in control samples was determined by serial dilutions followed by incubation at 37° C. for 24 hours. As illustrated in FIG. 5, The TiON fiber destroyed more than 80% of the bacteria, whereas Ag—TiON destroyed all of the bacteria.

(11) $Al_2O_3$ Fibers

Commercially available activated carbon coated fiber manufactured by Nippon Kynol (Kansai, Japan), with various surface areas, were used as templates. The activated carbon coated fibers used for this example were designated ACF7, ACF10, ACF15, ACF20 and ACF25, with BET surface areas of 690, 738, 1390, 1590 and 1960 $m^2/g$, respectively.

Activated carbon coated fiber was impregnated with an aqueous solution of $AlCl_3$, heat-dried at about 150° C., then heat-treated under $N_2$ at a temperature of about 600° C. A second heat treatment at 600° C. in air was then applied to remove the carbon template, and calcination of the product yielded thermally stable, white-colored $Al_2O_3$ fibers. The removal of the carbon template was confirmed by thermal gravimetric analysis (TGA).

Figure 6:
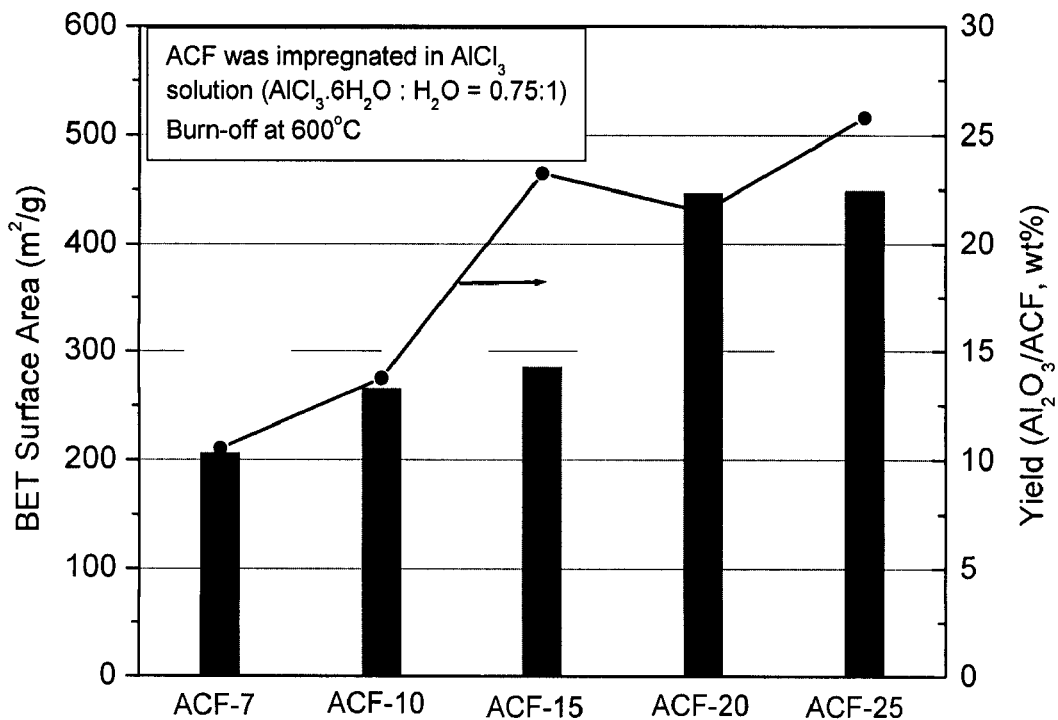
FIG. 6 illustrates the effect of ACF on surface areas and yield of $Al_2O_3$ fibers.
Figure 7:
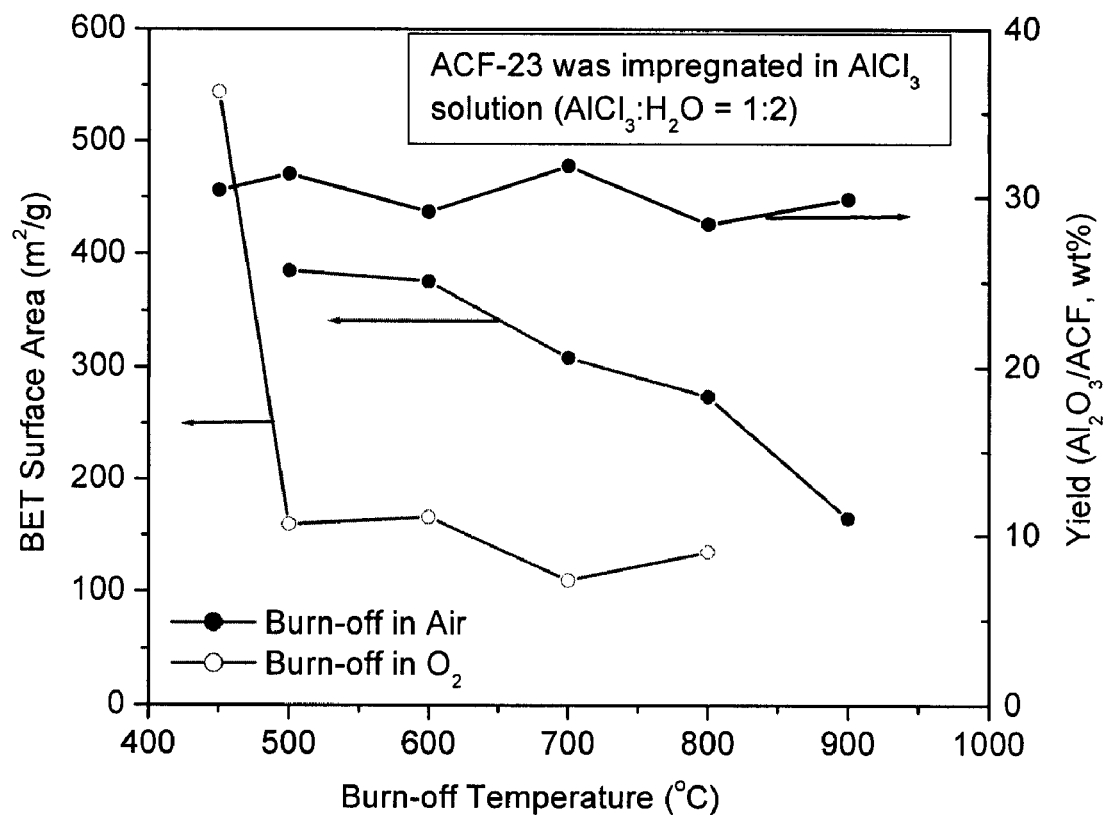
FIG. 7 illustrates the effect of the temperature of the second heating on the surface areas and the yield of $Al_2O_3$ fibers.
Figure 8:
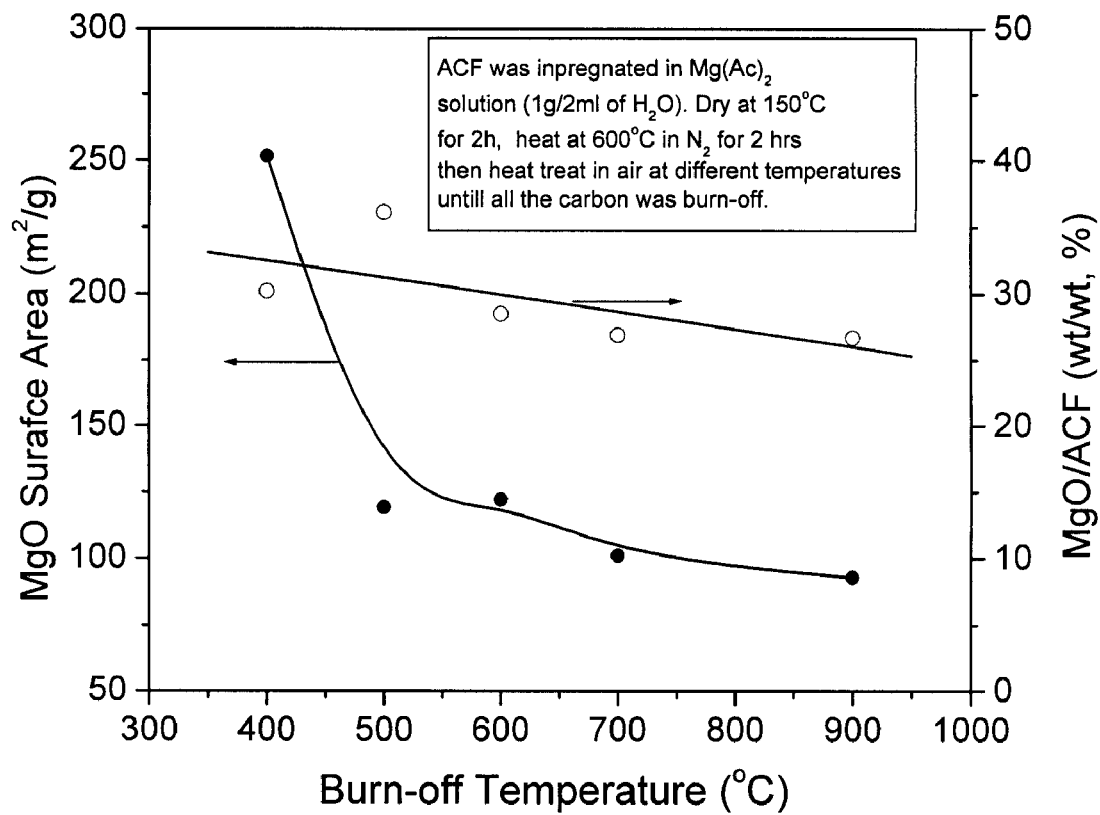
FIG. 8 illustrates the effect of the temperature of the second heating on the surface area and the yield of MgO fibers.

The $N_2$ absorption isotherms, the BET surface area and the pore size distribution of the product $Al_2O_3$ fibers were measured with an Autosor-1 (Quantachrome Corp., Boynton Beach, Fla.) volumetric sorption analyzer. As illustrated in FIG. 6, it appears that the BET surface area and the yield of $Al_2O_3$ fiber was directly proportional to the porosity of the ACF template. N, absorption isotherms at 77 K showed that the $Al_2O_3$ fibers were mesoporous materials, and pore distribution analysis showed peak values of mesopore in the range between 3.5 nm and 3.8 nm.

(12) Effect of Template-Removal Temperature on Product $Al_2O_3$ Fibers

ACF23 (surface area=1730 $m^2/g$) was impregnated with an aqueous solution of $AlCl_3$, heat-dried at about 150° C., then heat-treated under $N_2$ at a temperature of about 600° C. A second heat-treatment in air, at a temperature chosen from the range between 450° C. to 900° C., was applied to remove the carbon template. A thermally stable, white-colored $Al_2O_3$ fiber was then obtained upon calcination. The removal of the carbon template was confirmed by thermal gravimetric analysis (TGA), and the crystalline phases present in the fibers were identified by powder X-ray diffraction on a Rigaku D/max-VA (Rigaku/MSC, The Woodlands, Tex.).

Illustrated in FIG. 2 (7) are the effects of the carbon oxidation temperature on the surface area of the product fibers. At lower temperatures, for example 500° C., the complete removal of the template required usually more than 24 hours. At higher temperatures, for example 900° C., the template was completely removed within seconds. The BET surface area of the $Al_2O_3$ fibers was higher for lower template-removal temperatures, and when the temperature was 500° C. and above, heating in air yielded better results than in $O_2$. However, when the temperature was as low as 450° C., only $O_2$ could be used to remove all the carbon template, yielding a product with a very high BET surface area of above 500 $m^2/g$.

$N_2$ absorption isotherms showed that $Al_2O_3$ fibers obtained at different template-removal temperatures were all mesoporous materials. X-ray diffractometry revealed an amorphous structure for fibers obtained at a template removal temperature of 450° C., and more crystalline structures for higher template removal temperatures.

(13) MgO Fibers

ACF23 (surface area=1730 $m^2/g$) was impregnated in an aqueous solution of $Mg(Ac)_2$ obtained by dissolving 1 g of $Mg(Ac)_2$ in 2 mL of $H_2O$, heat-dried at about 150° C., and then heat-treated in $N_2$ at about 600° C. A second heat-treatment in air, at a temperature chosen from the range between 450° C. to 900° C., was applied to remove the carbon. Calcination of the product yielded thermally stable, white-colored MgO fibers. The $N_2$ absorption isotherms, the BET surface area and the pore size distribution of the product $Al_2O_3$ fibers were measured with an Autosor-1 (Quantachrome Corp., Boynton Beach, Fla.) volumetric sorption analyzer. The removal of the carbon was confirmed by thermal gravimetric analysis (TGA), and the crystalline phases present in the fibers were identified by powder X-ray diffraction on a Rigaku D/max-VA (Rigaku/MSC, The Woodlands, Tex.).

Illustrated in FIG. 3 (8) are the effects of the carbon removal temperature on the surface area and the yield of the MgO fiber products. At lower carbon removal temperatures, such as 400° C., longer periods of time were required to remove the carbon, and surface areas up to 250 $m^2/g$ were obtained. Higher carbon removal temperatures yielded fibers with lower surface areas. $N_2$ absorption isotherms showed that that all the product MgO fibers were mesoporous materials. X-ray diffractometry of the fibers revealed a cubic MgO crystal structure.

(14) $ZrO_2$ Fibers

Two samples of ACF23 (surface area=1730 $m^2/g$) were impregnated with a $Zr(NO_3)_4$ aqueous solution obtained by dissolving 1 g of $Zr(NO_3)_4$ in 5 mL of water, heat-dried at about 150° C., and then heat-treated in N, at about 600° C. The first sample was then heat-treated in air at 450° C., and the second sample was heat-treated in air at 600° C. The fibers were then calcinated, yielding thermally stable, white-colored $ZrO_2$ fibers.

The $N_2$ absorption isotherms, the BET surface area and the pore size distribution of the product $ZrO_2$ fibers were measured with an Autosor-1 (Quantachrome Corp., Boynton Beach, Fla.) volumetric sorption analyzer. The fibers obtained from the first sample has a BET surface area of 50 $m^2/g$, and the fibers obtained from the second sample had a BET surface area of 60 $m^2/g$. X-ray diffractometry of the fibers revealed a tetragonal $ZrO_2$ crystalline structure.

The invention claimed is:

1. A method of manufacturing a ceramic coated fiber, the method comprising:
    infiltrating an activated carbon coated fiber with a ceramic precursor, the infiltration being carried out at room temperature and comprising immersing the activated carbon coated fiber in a solution comprising the ceramic precursor in a volatile solvent;
    after the infiltrating, removing an excess of the ceramic precursor by washing with ethanol; and
    after the removing, heat treating the activated carbon coated fiber containing the ceramic precursor to form a ceramic coated fiber.

2. The method of claim 1, wherein the heat treating comprises:
    a first heating at a first temperature of at least 250° C., to cure the ceramic precursor, and
    a second heating at a second temperature of at least 400° C. in an oxidizing atmosphere to remove the carbon.

3. The method of claim 2, wherein the first heating is in an inert atmosphere.

4. The method of claim 2, wherein the ceramic comprises $TiO_2$ and/or TiON having an anatase structure.

5. The method of claim 4, wherein the ceramic precursor further comprises a nitrogen or sulfur dopant.

6. The method of claim 5, wherein the nitrogen source is tetramethylammonium hydroxide.

7. The method of claim 2, further comprising:
    contacting the ceramic coated fiber with a compound containing silver; and a third heating of the ceramic coated fiber.

8. The method of claim 2, further comprising:
    contacting the ceramic coated fiber with a compound containing palladium;
    a third heating of the ceramic coated fiber; and
    a fourth heating of the ceramic coated fiber in an atmosphere comprising $H_2$.

9. The method of claim 2, wherein the ceramic comprises crystalline ceramic and has a BET surface area of at least 50 $m^2/g$.

10. The method of claim 2, wherein the ceramic comprises at least one member selected from the group consisting of $TiO_2$, TiON, TiOS, $Al_2O_3$, $ZrO_2$, and MgO.

11. The method of claim 2, where the oxidizing atmosphere is pure $O_2$.

12. The method of claim 2, where the oxidizing atmosphere is air.

13. The method of claim 2, where the first temperature is from 250° C. to 600° C.

14. The method of claim 13, where the first temperature is from 250° C. to 400° C.

15. The method of claim 2, wherein the second temperature is from 400° C. to 1000° C.

16. The method of claim 1, further comprising, prior to the heat treating, hydrolyzing the ceramic precursor.

17. The method of claim 16, where hydrolyzing the ceramic precursor comprises exposing the ceramic precursor to air moisture.

18. A method for manufacturing an intermediate for the fabrication of ceramic coated fibers, the method comprising
    infiltrating an activated carbon coated fiber with a ceramic precursor, the infiltration being carried out at room temperature and comprising immersing the activated carbon coated fiber in a solution comprising the ceramic precursor in a volatile solvent;
    after the infiltrating, removing an excess of the ceramic precursor by washing with ethanol; and
    after the removing, heating the activated carbon coated fiber containing the ceramic precursor to cure the precursor.

* * * * *